United States Patent [19]

Kaye et al.

[11] Patent Number: 5,327,777
[45] Date of Patent: Jul. 12, 1994

[54] BIORHEOLOGICAL MEASUREMENT

[75] Inventors: Paul H. Kaye, Kimpton; Mark Tracey, Mount Pleasant, both of United Kingdom

[73] Assignee: University of Hertfordshire, United Kingdom

[21] Appl. No.: 920,589
[22] PCT Filed: Feb. 22, 1991
[86] PCT No.: PCT/GB91/00289
 § 371 Date: Aug. 21, 1992
 § 102(e) Date: Aug. 21, 1992
[87] PCT Pub. No.: WO91/13338
 PCT Pub. Date: Sep. 5, 1991

[30] Foreign Application Priority Data

Feb. 24, 1990 [GB] United Kingdom ............... 9004219
Jul. 17, 1990 [GB] United Kingdom ............... 9004235
Jul. 17, 1990 [GB] United Kingdom ............... 9015643

[51] Int. Cl.$^5$ ............................................. G01N 11/04
[52] U.S. Cl. ........................................ 73/54.06; 73/54.09
[58] Field of Search ................. 73/54.01, 54.04, 54.05, 73/54.06, 54.09, 54.11; 356/39, 40

[56] References Cited

U.S. PATENT DOCUMENTS

| | | | |
|---|---|---|---|
| 4,449,395 | 5/1984 | Kurtz et al. | 73/54.11 |
| 4,519,239 | 5/1985 | Kiesewetter et al. | 73/55 |
| 4,522,494 | 6/1985 | Bonner | 356/39 |
| 4,858,127 | 8/1989 | Kron et al. | 73/54.09 |
| 4,884,437 | 12/1989 | Constant et al. | 73/54.01 |

FOREIGN PATENT DOCUMENTS

| | | | |
|---|---|---|---|
| 0094576 | 11/1983 | European Pat. Off. | 73/55 |
| 0368241 | 5/1990 | European Pat. Off. | |
| 3802221 | 7/1989 | Fed. Rep. of Germany | |
| 2162954 | 2/1986 | United Kingdom | |

OTHER PUBLICATIONS

Abstracts: Japanese Society of Biorheology, vol. 26, No. 6, 1055.
Y. Kikuchi et al., "Microchannels made on silicon wafer for measurment of flow properties of blood cells".
E. Ogura et al., "Measurement of Red Blood Cell Deformability using a single micropore on a thin $Si_3N_4$ film", Japan, Oct. 1988, in Japanese.
(E. Ogura et al., "Measurement of Red Blood Cell Deformability using a single micropore on a thin $Si_3N_4$ film", revised and republished in English, I.E.E.E. Transactions on Biomedical Engineering, vol. 38, No. 8, Aug. 1991.)
Cryogenics, vol. 23, No. 5, May 1983, (Guildford, Surrey, GB) W. Peiyi et al.: "Measurement of friction factors for the flow of gases in very fine channels used for microminiature joule–Thomson refrigeratores", pp. 273–277.

Primary Examiner—Hezron E. Williams
Assistant Examiner—Valerie Francies
Attorney, Agent, or Firm—Davis, Bujold & Streck

[57] ABSTRACT

A method of performing biorheological measurements on a suspension (4) of cells by causing some of the cells to pass through one or more microsize tunnels (3) in a solid medium (1, 2) under a pressure difference between the tunnel ends and monitoring (6) their passage through the tunnel or tunnels, characterized in that the pressure difference is monitored to produce a signal which is recorded or is utilized to provide feedback to regulate the biorheological measurements. Apparatus for performing this method may have such a pressure feedback control, or may have tunnels with at least partly transparent walls for transmitting optical information to a detector for the biorheological measurements.

9 Claims, 4 Drawing Sheets

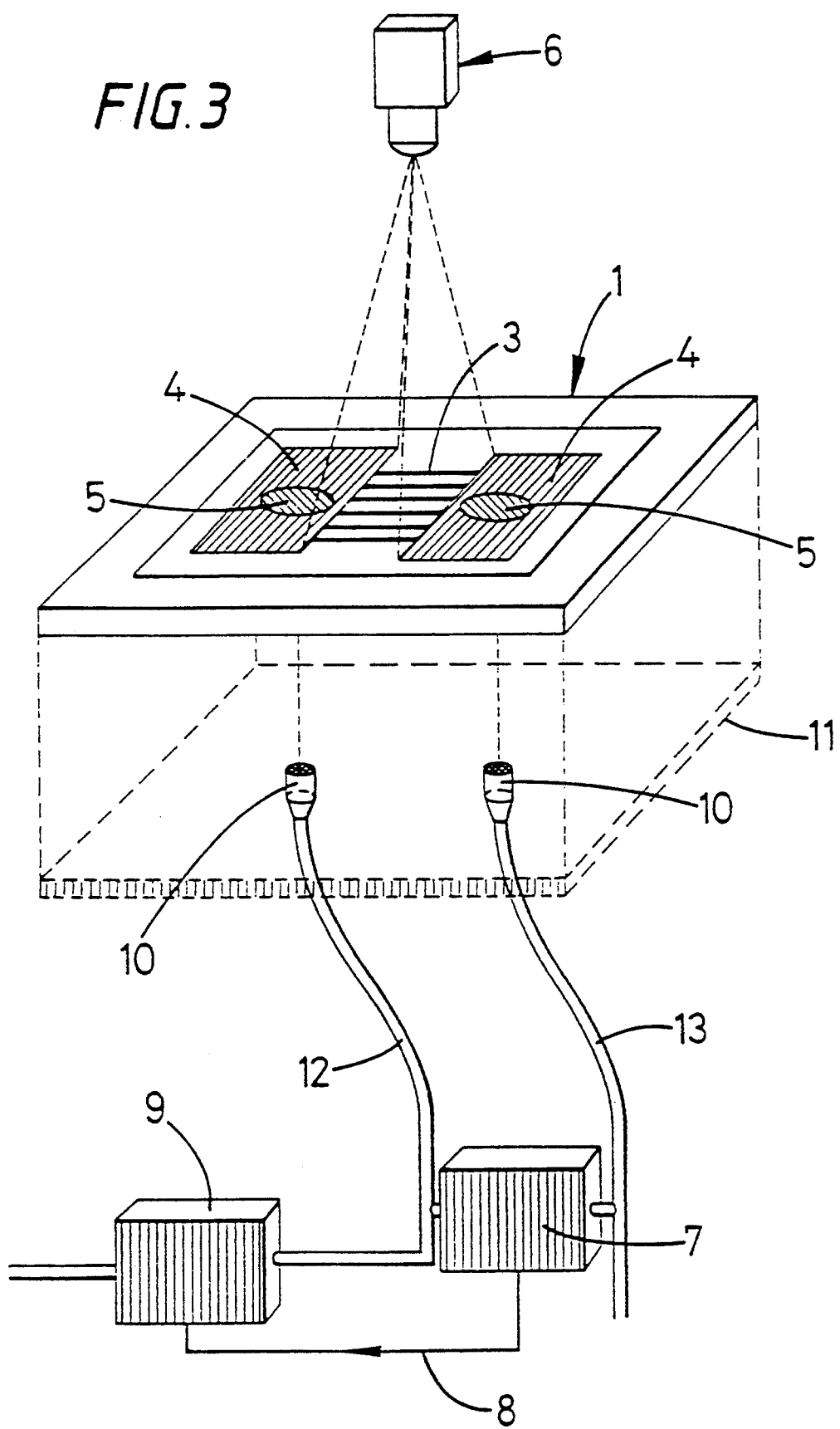

BIORHEOLOGICAL MEASUREMENT

This invention relates to the measurement of biological cell rheological properties and to apparatus for use in such measurement.

The rheology of biological cells is of considerable interest to workers in the medical and pharmaceutical fields. Of particular interest is the sub-discipline of microrheology. This concerns inter alia the flow of cells in channels having dimensions approaching those of the cells themselves. One example of this is the flow of human red and white blood cells in the capillary networks of the human body. In these vessels cells transit serially while undergoing deformation due to the capillary diameter being less than the cell diameter. The degree of the cells' deformability is related to the elastic constants of the cells which are, in turn, related to biochemical properties of the cells. It is suggested that some disease states can affect the biochemistry and hence deformability of the cell, and in doing so symptoms of circulatory disease result. For example, the disease "Diabetes Mellitus" can result in progressive circulatory dysfunction; this is believed to be contributed to by a change in erythrocyte cellular deformability.

Due to the extreme difficulty of in-vivo measurement of these properties recourse is made to in-vitro techniques. Unfortunately the rheological properties of cell suspensions make it impossible to determine accurately microrheological characteristics from macrorheological measurements. In an attempt to overcome this, several techniques have been developed to measure cells passing through fabricated microchannels. Potentially the most accurate of these existing techniques is to pass cells individually through glass micropipettes while measuring their flow properties.

Micropipettes have offered the most physiologically analogous technique, but several problems have restricted their application. These fall into two groups. Firstly, fabrication and utilization related factors limit measurement accuracy. Secondly, due to several factors the number of cells of one sample that can be measured is statistically too small for detailed analysis. The latter limitation precludes the use of this technique, in its current implementation, for the identification of small sub-populations of cells with aberrant rheological properties.

Macroscopic filtration techniques have been recognized as an alternative, and have been developed in parallel, but there have been problems of reproducibility of results, due to the differences in diameter between different pores of the same membrane and between different membranes. Some refined forms of filtrometer, the Single Erythrocyte Rigidometer (SER) and its lineal development, the Cell Transit Analyser (CTA) overcome the intra analysis reproducibility problem by means of a continuous flow technique through one or more pores in a membrane. Furthermore, operator effects are virtually removed by automating the erythrocyte transit measurement. We categorize the CTA as a Multi Channel Non Concurrent Transit device (MCNCT). The CTA and SER do, however, suffer from the drawback that it is impossible in current devices to differentiate between the steady state flow of an erythrocyte within a pore in the membrane and entrance effects as the erythrocyte initially deforms to enter the pore: only a global 'occlusion time' is measured, i.e. the time taken for a cell to pass through the pore and re-appear on the other side. This drawback is related to the difficulty of fabricating a device of this form that offers a means of monitoring the cells' "velocity profile" during the "transit" as distinct from measuring the global "occlusion time".

A further disadvantage of MCNCT devices is that they do not offer a higher cell throughput than an SER. This is due to the potential ambiguities that would result from concurrent transits being monitored as a composite signal. As a result only one pore of the MCNCT can contain a cell at given time. This is achieved by using a low haematrocrit of about 10 and attempting to reject occasional multiple transits by an appropriate hardware or software algorithm. The main advantage of MCNCT devices is that they are tolerant of clogging, rather than suddenly ceasing measurement as is the case in a micropipette or SER.

A recently-developed CTA is described by Koutsouris D., Guillet R., Lelivre J. C., Guillemin M. T., Beuzard Y. 1986: Mechanical properties of the erythrocytes indicated by cell transit time analysis. 6th International Congress of Biorheology, Vancouver 1986.

The object of the present invention is to overcome the aforesaid problems. Accordingly, the invention provides a method of performing biorheological measurements. The tunnel(s) may be formed in the substrate to a high precision utilizing a micromachining technique, which uses modified integrated circuit fabrication processes to generate physical structures, in conjunction with other processes.

Advantageously, a pair of reservoirs for the suspension of cells is formed in the solid medium, with the tunnels extending between the reservoirs.

The location or transit speed of cells in the tunnel(s) at any instant may be recorded by imaging or by direct measurement by transducers or sensors such as charge sensors, integral with or adjacent to the solid medium. With a knowledge of the tunnel dimensions, rheological parameters may be calculated.

The invention also provides apparatus for performing biorheological measurements.

It will be appreciated that the invention combines the facility for automation and the physical parallelism of the CTA with the observability of the micropipette. In addition, the possibility of introducing constrictions in the tunnels, previously impossible with pores in a filter membrane, now exists and will enable new types of measurement to be made. These properties may be achieved for example by implementing a planar array of high precision capillaries as a microfabricated silicon flow cell. The design and fabrication techniques employed in such a capillary array overcome many of the difficulties associated with micropipettes. The class of devices to which such a flow cell belongs will be referred to as "Multi-Channel Multiple Concurrent Transit": MCMCT.

In making the aforesaid measurements, a pump may be required to create the pressure difference to move the cells along the tunnel(s). Such a pump has to be capable of pumping a defined, small, quantity of fluid less than $100\mu$ liters in a manner free of discontinuities.

Delivery of very low volumes of fluid in a time-continuous manner is a recognised problem in science, medicine and technology. An example of a conventional approach is the use of stepper motor driven syringes. This technique, by its nature, results in a microscopically discontinuous pumping action. Furthermore, both static and kinetic friction, or stiction effects between the syringe bore and plunger seal can result in further discontinuities.

In another aspect the present invention relates to a pump. In use the reservoir is pre-charged with the fluid to be pumped, and the piezoelectrically-generated force is applied; as a result the fluid is pumped from the reservoir, for example, via an orifice which may be provided at an appropriate location. The use of a piezoelectric element yields a continuous input/output function.

The invention will now be further described by way of example with reference to the accompanying schematic drawings, not drawn to scale, in which:

FIG. 3 is a partly exploded perspective view of a measuring system utilising the apparatus of FIGS. 1 and 2;

Figure 1:
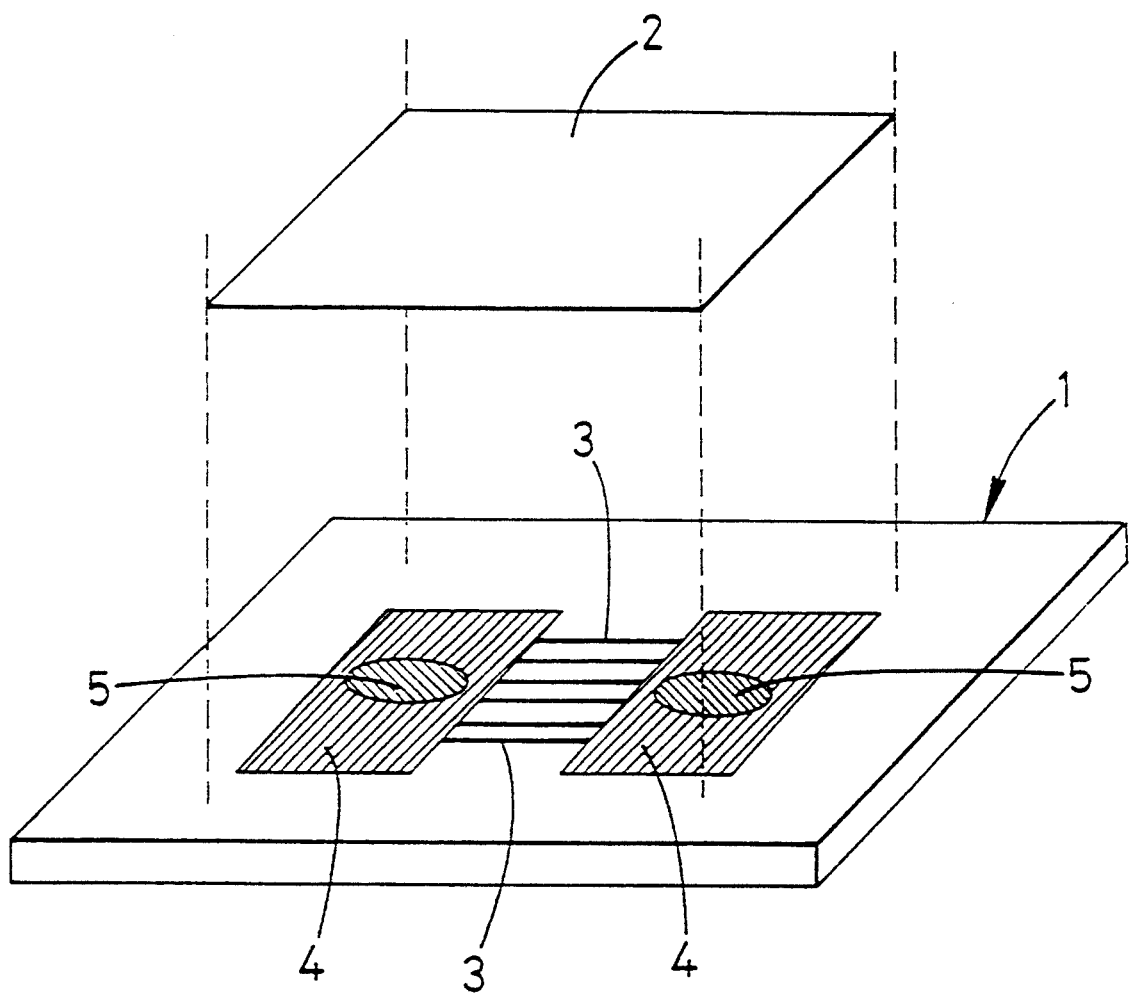
FIG. 1 is an exploded perspective view of one form of apparatus for carrying out measurements in accordance with the invention.

Referring now to the drawings, in which corresponding parts are denoted by identical reference numerals, the apparatus shown in FIG. 1 comprises a silicon substrate 1 and a thin glass cover slip 2 which could typically be 300 micro meters thick. A number of equal-length parallel channels 3 with square base edges and constant cross-section and of appropriate dimensions are chemically etched into the upper surface (as seen in FIG. 1) of the substrate 1. The parallel channels terminate in reservoir structures 4 also etched into the upper surface of the substrate 1. Outlet holes 5 connect the centre of the reservoir structures 4 with the lower surface (as seen in FIG. 1) of the substrate. Typical dimensions for the substrate would be 5 mm long by 4 mm wide and the length of the channels 3 could typically be 100 $\mu$m.

The thin cover slip 2 is placed over the channels 3 and reservoirs 4 so that the channels 3 in effect become tunnels. The cover slip 2 is pressed into intimate contact with the substrate 1 by gas pressure. Alternatively it could be permanently sealed to the substrate 1. The channels 3, reservoirs 4 and holes 5 thus form a continuous chamber closed except for the orifices on the lower surface of the substrate provided by the holes 5.

Figure 2:
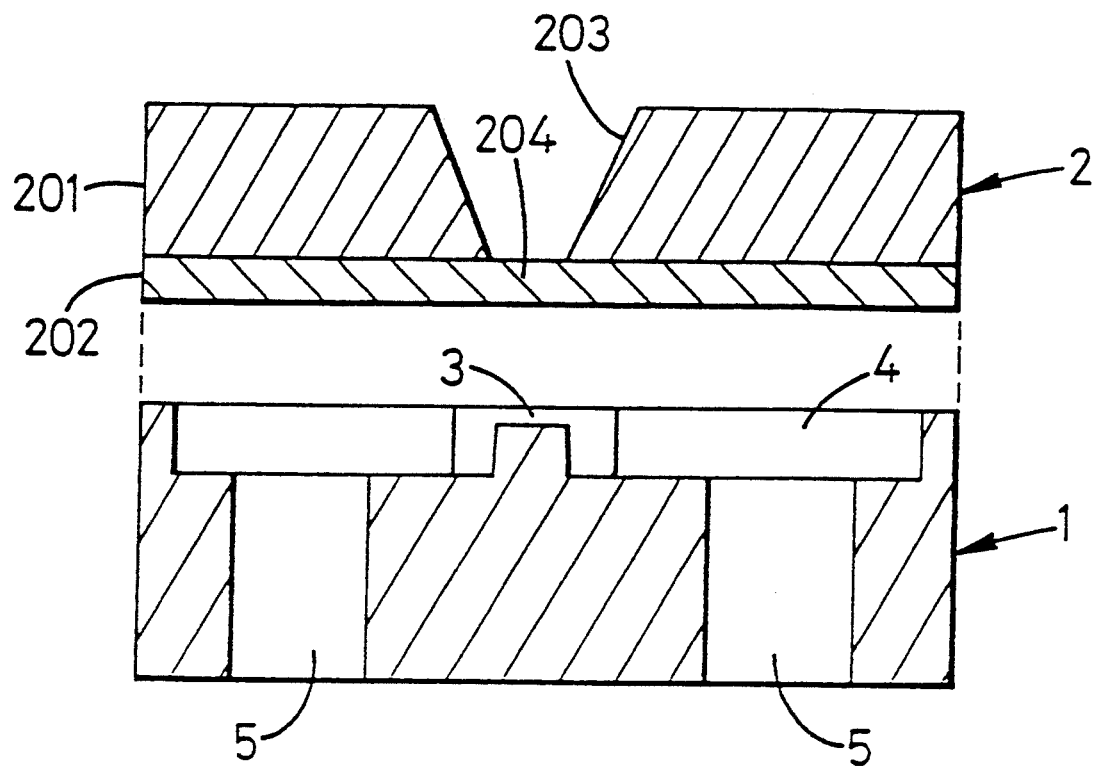
FIG. 2 is a sectional view of part of the apparatus of FIG. 1, in a modified form, and to a larger scale.

The modified apparatus of FIG. 2 is similar in most respects to that of FIG. 1, the measurement cell fabricated using the emerging technology of silicon micromachining. The device consists of two layers of silicon substrates 1,2 bonded together.

Fabrication is commenced on the lower element 1 which has an array of channels 3 chemically etched into the surface. Channels have been made in a range of cross-sectional dimension options, however 5 $\mu$m $\times$ 5 $\mu$m has been used for preliminary evaluation. These dimensions are to sub-micron tolerances, and presently have an intra device accuracy of <100 nm and an inter device accuracy of <200 nm. The cross-sectional profile of the first prototypes is square with filleted bottom corners, but it will have a curved profile, e.g. cylindrical, in future development. The channels are 100 $\mu$m in length. These dimensions have been chosen to mimic a typical physiological capillary in body tissue. The array of channels is terminated at both ends with reservoir structures 4, of approximately 15 $\mu$m depth. In the centre of each reservoir 4, a deep shaft 5 has been etched through to the lowermost surface of the silicon.

The upper layer 2 of silicon, which replaces the glass cover slip of FIG. 1, is prepared by chemically growing a layer 202 of transparent silicon dioxide on the surface of a silicon substrate 201. Then an opening 203 in the form of a shaft is etched to the interface between the silicon dioxide 202 and silicon 201 of the upper layer. The substance used for this etch does not react with silicon dioxide and hence yields an SiO2 "window" in a Si "frame". The window is dimensioned and positioned to yield a view of the channels 3 when the two elements 1,2 of silicon are combined.

The final stage of preparation involves the alignment and atomic bonding of the adjacent, clean, surfaces of the two layers. In this process the channels are converted to capillaries with transparent faces formed by the window.

The resulting flow cell measures approximately 4$\times$5 mm and is precisely mounted on a carrier 11 complete with two capillary feed tubes 12, 13 as shown in FIG. 3.

In use of the apparatus of FIGS. 1 and 2, red blood cells (in this example only) in suspension in the reservoir 4 are introduced into tunnel openings in a random orientation, undergoing deformation, and are fed along the tunnels formed by the channels 3, a process which may take 2-3 seconds. The cell positions in the tunnels are monitored by optical imaging via a video camera 6 as shown in FIG. 3. The capillary array is imaged via an incident illumination (metallurgical) microscope. In order to optimise the contrast ratio between the cell and channel, 400 nm illumination in the far visible violet is used. This wavelength is absorbed by the haemoglobin in erythrocytes. As a result the erythrocytes are contrasted as dark objects against the highly reflective light background of the silicon. The resulting image is converted to an analogue electrical signal by the video camera 6 and subsequently digitised by a 256$\times$256 pixel video digitiser. The resulting data is fed to a computer for image processing. The output of the camera is processed such that the temporally coincident movements of cells in separate tunnels can be monitored concurrently, and so that any tunnels that are, or have been, blocked are ignored. The windows 204 may extend over a major part of the tunnel length, or over its entire length as shown.

A differential pressure sensor 7 provides a signal that is used in a control loop 8 to regulate the flow rate of fluid via a flow regulating device 9 in order to maintain a constant pressure differential between the inlets and outlets of the tunnels. In this manner, interaction between cells in separate tunnels due to the flow rate differences between the tunnels induced by the presence or absence of cells is eliminated. The deformability of cells is calculated utilising the spatial information from the camera, the time reference from within the associated instrumentation, the predetermined tunnel geometry, and the constant regulated pressure differential across the tunnels. The pressure difference is typically in the physiological range of (2–20) mm H$_2$O; accuracy over this range is achievable using a discrete silicon diaphragm differential, or absolute, fluid pressure transducer.

Figure 4:
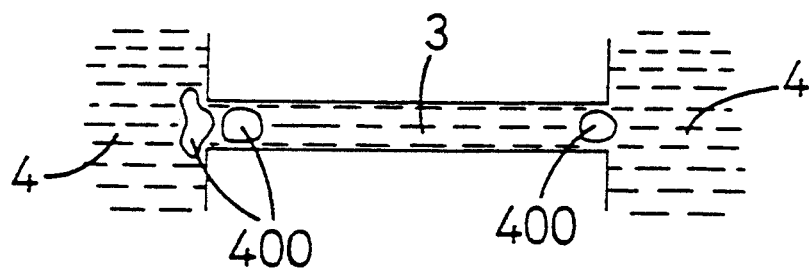
FIG. 4 is a diagram of a single tunnel, showing different stages of the passage of a cell along the tunnel.

FIG. 4 shows a blood cell 400 entering a channel 3 under the pressure differential, slowly deforming as it does so. The reverse process of expansion occurs on exit. Consequent variation of its speed at different stages may be monitored, as may its actual volume be determined. In alternative forms of channels, there may be a variation of cross-section along its length, such as an intermediate constriction (see FIG. 2), or the channels may have different configurations from one another.

One method of introducing fluid i.e. a cell suspension to the apparatus is illustrated in FIG. 3. In this implementation the substrate 1 forms a fluid tight seal with a support plate 11 (shown in dotted line, separated from the substrate) through which holes 10 have been formed. The holes 10 are positioned so that they align with the holes 5 in the substrate. The thickness of the plate 11 is such that it enables the connection of capillary pipes or tubing 12 and 13 to the holes 10 through appropriate connectors.

Figure 5:
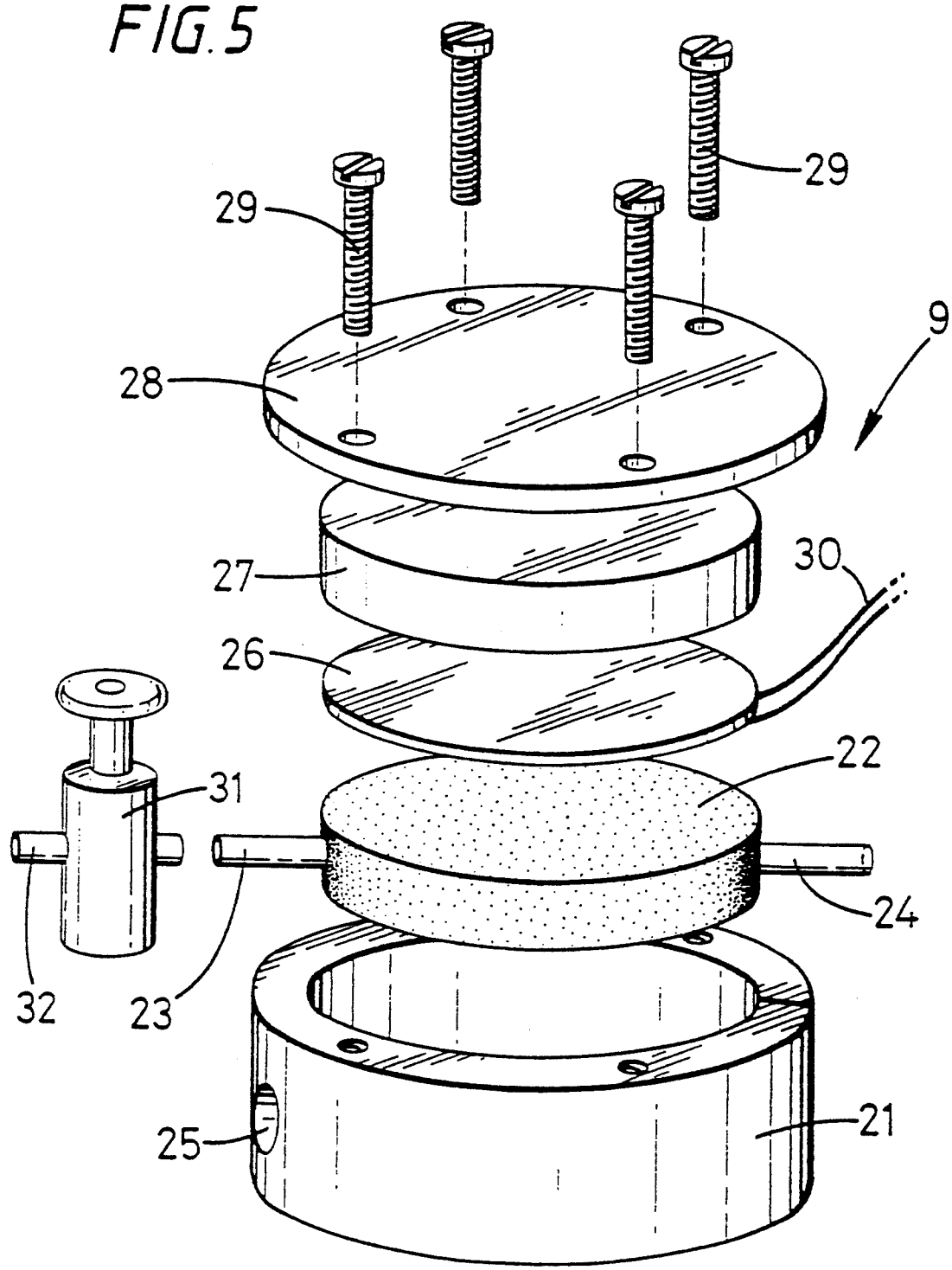
FIG. 5 is an exploded perspective view of a piezoelectric pump which can be used as one of the elements in the system of FIG. 3.

One advantageous form for the flow regulating device 9 is the piezoelectric pump shown in FIG. 5. This pump comprises a rigid cylindrical casing 21 with a closed lower end (in the orientation of FIG. 5). A deformable reservoir 22 is contained within the casing and this has inlet and outlet tubes 23 and 24 which extend through diametrically opposite holes 25 in the casing 21. A disc 26 of piezoelectric material fits on top of the reservoir 22 and within the casing 21. A spacer 27 fits over the disc 26 and within the casing 1. The upper end of the casing 21 is closed by a cover plate 28 which is secured in position by bolts 29 to maintain the components in the casing 21 in correct alignment. The disc 26 is provided with an electrical control voltage through electrical leads 30 passing through the wall of the casing 21.

In operation the reservoir 22 is charged via a valve 31 which allows fluid to enter from inlet tube 32. While the reservoir 22 is being charged no deforming force is applied by the piezoelectric disc 26. When charging is complete the valve 31 is closed and a voltage is applied to the piezoelectric disc resulting in its extension and in deformation of the reservoir 22, hence pumping.

The reservoir 22, being a separate self-contained item, can be supplied as a disposable item suitable for use with hazardous materials or materials where interpump cycle contamination cannot be tolerated. The reservoir 22 may be formed as a flat spiral of deformable tubing.

Use of a spacer plate of greater area than the piezoelectric disc disposed between the disc and the reservoir will increase the area over which the piezoelectric force acts. Hence the pumped volume for a given piezoelectric disc might be increased to a limit determined by other parameters.

We claim:

1. A method of performing biorheological measurements on a suspension of cells by causing some of the cells to pass through at least one tunnel in a solid medium under a pressure difference between the tunnel ends and monitoring their passage through the tunnel, wherein the tunnel is of a diameter such as to deform each successive cell passing through it whereby the measurements are performed on a cell-by-cell basis; the pressure difference is monitored to produce a signal which is at least one of a) recorded and b) utilized to provide feedback to regulate the biorheological measurements; and the passage of successive cells through the tunnel is observed using a detector effective over at least a majority of the length of the tunnel to determine the velocity of motion of each cell at two or more stages of its passage into, through and out of the tunnel.

2. A method according to claim 1, in which the pressure difference signal is utilized to provide feedback to control the pressure difference so as to maintain a pressure difference constant.

3. A method according to claim 1, wherein several tunnels are provided and the cells are drawn from a common reservoir into each of said several tunnels, all under the same pressure difference.

4. A method according to claim 3, in which the tunnels are of different configurations.

5. Apparatus for performing biorheological measurements on a suspension of cells, comprising a solid medium (1,2) having therein at least one tunnel (3) communicating with a reservoir (4) for the cell suspension, and means (9) for applying a pressure difference between the ends of the tunnel, wherein at least one portion (204) of a wall of the tunnel (3) is transparent to a range of optical wavelengths for at least a majority of the length of the tunnel, and detector means (6) associated with the tunnel, responsive to optical information transmitted through the transparent part from within the tunnel, for observing the passage of the cells; the tunnel having at least two portions with different cross-sections, thereby providing different constrictions to the flow of a cell within the tunnel, for comparing the behavior of the cells passing through such portions.

6. Apparatus according to claim 5 comprising a plurality of tunnels (3) communicating with a reservoir (4) for the cell suspension, first means (9) which applies a pressure difference between the ends of each tunnel, and second means (7) responsive to the applied pressure difference to produce a signal (8) which is utilized to provide feedback to the first means (9) to maintain a predetermined constant pressure difference; at least one of the tunnels having at least two portions with different cross-sections, thereby providing different constrictions to the flow of a cell therein, for comparing the behavior of the cells passing through such portions.

7. Apparatus according to claim 5, in which the tunnels extend into one or more crystalline substrates (1,2).

8. Apparatus according to claim 6, in which the tunnels extend into one or more crystalline substrates (1,2).

9. The apparatus according to claim 6, further comprising a pump for creating the pressure difference to move the cells along the tunnels wherein the pump is capable of delivering predetermined volumes of fluid and the pump comprises a deformable fluid reservoir (22) constrained from isovolumetric deformation, comprising a piezoelectric drive element (26) adjacent the reservoir for deforming the reservoir, in response to an electric drive potential (30), in a time-continuous manner, smoothly to change its volume thereby to expel fluid therefrom.

* * * * *